US 6,721,585 B1

(12) United States Patent
Parker

(10) Patent No.: US 6,721,585 B1
(45) Date of Patent: *Apr. 13, 2004

(54) UNIVERSAL MODULAR PULSE OXIMETER PROBE FOR USE WITH REUSABLE AND DISPOSABLE PATIENT ATTACHMENT DEVICES

(75) Inventor: Brent Parker, Murrieta, CA (US)

(73) Assignee: Sensidyne, Inc., Clearwater, FL (US)

( * ) Notice: Subject to any disclaimer, the term of this patent is extended or adjusted under 35 U.S.C. 154(b) by 77 days.

This patent is subject to a terminal disclaimer.

(21) Appl. No.: 09/931,273

(22) Filed: Aug. 17, 2001

Related U.S. Application Data

(63) Continuation-in-part of application No. 09/758,038, filed on Jan. 11, 2001, and a continuation-in-part of application No. 09/679,828, filed on Oct. 5, 2000, now Pat. No. 6,519,487, which is a continuation-in-part of application No. 09/417,898, filed on Oct. 14, 1999, now Pat. No. 6,343,224, and a continuation-in-part of application No. 09/352,144, filed on Jul. 13, 1999, now Pat. No. 6,321,100, which is a continuation-in-part of application No. 09/289,647, filed on Apr. 12, 1999, now Pat. No. 6,144,868.

(60) Provisional application No. 60/104,332, filed on Oct. 15, 1998.

(51) Int. Cl.⁷ ................................................ A61B 5/00
(52) U.S. Cl. ........................................ 600/344; 600/310
(58) Field of Search ................................. 600/310, 322, 600/323, 340, 344

(56) References Cited

U.S. PATENT DOCUMENTS

| | | | |
|---|---|---|---|
| 4,685,464 A | | 8/1987 | Goldberger et al. |
| 4,830,014 A | | 5/1989 | Goodman et al. |
| 5,094,240 A | | 3/1992 | Muz |
| 5,170,786 A | | 12/1992 | Thomas et al. |
| 5,249,576 A | | 10/1993 | Goldberger et al. |
| 5,337,744 A | | 8/1994 | Branigan |
| 5,387,122 A | | 2/1995 | Goldberger et al. |
| 5,437,275 A | | 8/1995 | Amundsen et al. |
| 5,452,717 A | | 9/1995 | Branigan et al. |
| 5,645,440 A | | 7/1997 | Tobler et al. |
| 5,673,693 A | | 10/1997 | Solenberger |
| 5,782,757 A | | 7/1998 | Diab et al. |
| 5,817,010 A | | 10/1998 | Hibl |
| RE36,000 E | | 12/1998 | Swedlow et al. |
| 6,144,868 A | * | 11/2000 | Parker .................. 600/344 |
| 6,343,224 B1 | * | 1/2002 | Parker .................. 600/344 |
| 6,519,487 B1 | * | 2/2003 | Parker .................. 600/344 |

* cited by examiner

Primary Examiner—Eric F. Winakur
(74) Attorney, Agent, or Firm—Jim Zegeer

(57) ABSTRACT

A system and method of standardizing modular probe housings so that the standardized probe housings may be incorporated into probes adapted to work with at least one of a multiplicity of manufacturers' oximeters. The probe housings are adapted to matingly engage at least a disposable bandage apparatus and a reusable finger attachment device.

7 Claims, 3 Drawing Sheets

UNIVERSAL MODULAR PULSE OXIMETER PROBE FOR USE WITH REUSABLE AND DISPOSABLE PATIENT ATTACHMENT DEVICES

REFERENCE TO RELATED APPLICATIONS

This application is a continuation-in-part of application Ser. No. 09/417,898 filed Oct. 14, 1999 entitled REUSABLE PULSES OXIMETER PROBE AND DISPOSABLE BANDAGE APPARATUS now U.S. Pat. No. 6,343,224, which in turn is a continuation-in-part of Ser. No. 09/289,647 filed Apr. 12, 1999 entitled REUSABLE PULSE OXIMETER PROBE AND DISPOSABLE BANDAGE APPARATUS and now issued as U.S. Pat. No. 6,144,868, and is a continuation-in-part application of Ser. No. 09/679,828 filed Oct. 5, 2000 now U.S. Pat No. 6,519,487; and is a CiP of Ser. No. 09/352,144 filed Jul. 13, 1999 and is CiP of now U.S. Pat. No. 6,321,100; Ser. No. 09/758,038 filed Jan. 11, 2001; each of which is incorporated herein by reference. This application claims benefit of U.S. provisional application No. 60/104,332 filed Oct. 15, 1998.

BACKGROUND OF THE INVENTION

Heretofore the use of pulse oximeter probes has been limited to the use of a costly, reusable probe, which is contaminated by use on a patient, or cheaper, single-use probes, which, in the aggregate, amount to a considerable expenditure for a healthcare institution. The current applicant in his U.S. Pat. No. 6,144,868, and subsequent continuations-in-part, has described a reusable pulse oximeter probe to be used with a disposable bandage apparatus. With this device, the costly reusable portion of the probe is isolated from the patient by means of an inexpensive bandage apparatus. This allows the caregiver to dispose of the inexpensive bandage apparatus while retaining the more costly, reusable portion of the probe. The reusable probe can then be used in conjunction with another disposable bandage apparatus on another patient.

Despite the cost and safety advantages of the reusable probe and disposable bandage apparatus over disposable probes, an increasing number of institutions are beginning to utilize reusable finger clip probes because of the cost savings associated with a completely reusable product. Despite the discomfort of these devices and the risk of spreading infection from patient to patient, the trend toward reusable probes continues to strengthen.

However, in all institutions there is always the need for some disposable probes. Patients who have compromised immune systems, surgical patients, where sterility is important, and neonatal and pediatric patients, where the size of the appendage to be monitored is too small for finger clips, require the use of disposable probes or a disposable bandage apparatus.

Clearly, it would be advantageous to offer a universal, modular, reusable probe that could be used in conjunction with either a reusable finger attachment device or a disposable bandage apparatus, each having receptacles into which the reusable probe could be lockingly engaged and disengaged. In addition, probes from all the different oximeter manufacturers could be standardized so that they could be used in conjunction with these same patient attachment devices.

THE PRESENT INVENTION

The present invention is directed to a system and a method of standardization of a pulse oximeter probe wherein the probe comprises at least one light emitting diode and at least one photocell detector wherein said emitter and detector are incorporated into modular plastic housings, at least one housing having an aperture or radiation transparent window aligned with said emitter, and at least said second housing having an aperture or radiation transparent window aligned with said detector; wherein said housings can lockingly engage and disengage receptacles mounted on at least either:

(a) a reusable finger attachment device, or (b) a disposable bandage apparatus, and transmit and receive light through the appendage of a patient when either of the above devices are attached to a patient and when the housings of said probe are matedly engaged with the receptacles of the attached device.

The receptacles of the disposable bandage apparatus or the reusable finger attachment device may have locking levers for lockingly engaging and disengaging the modular probe housings.

The probe housings may have indentations or detentes for lockingly engaging and disengaging the levers of the receptacles of the disposable bandage apparatus or reusable finger attachment device.

The disposable bandage apparatus may have radiation transparent windows for the isolation of the probe housings from the patient.

The probe housings may be standardized in size so that probes to fit at least one of a multiplicity of manufacturers' oximeters will incorporate housings that can be matedly engaged with either a reusable finger attachment device or a disposable bandage apparatus.

What is disclosed is the method of supplying pulse oximeter probes compatible with at least one of a multiplicity of manufacturers' oximeters, said probe or probes incorporating standardized probe housings, which can be matedly engaged with at least either a reusable finger attachment device or a disposable bandage apparatus.

DESCRIPTION OF THE DRAWINGS

The above and other advantages of the invention will become more clear when considered with the following specifications and accompanying drawings wherein.

DESCRIPTION OF THE MODULAR PULSE OXIMETER PROBE

Figure 1:
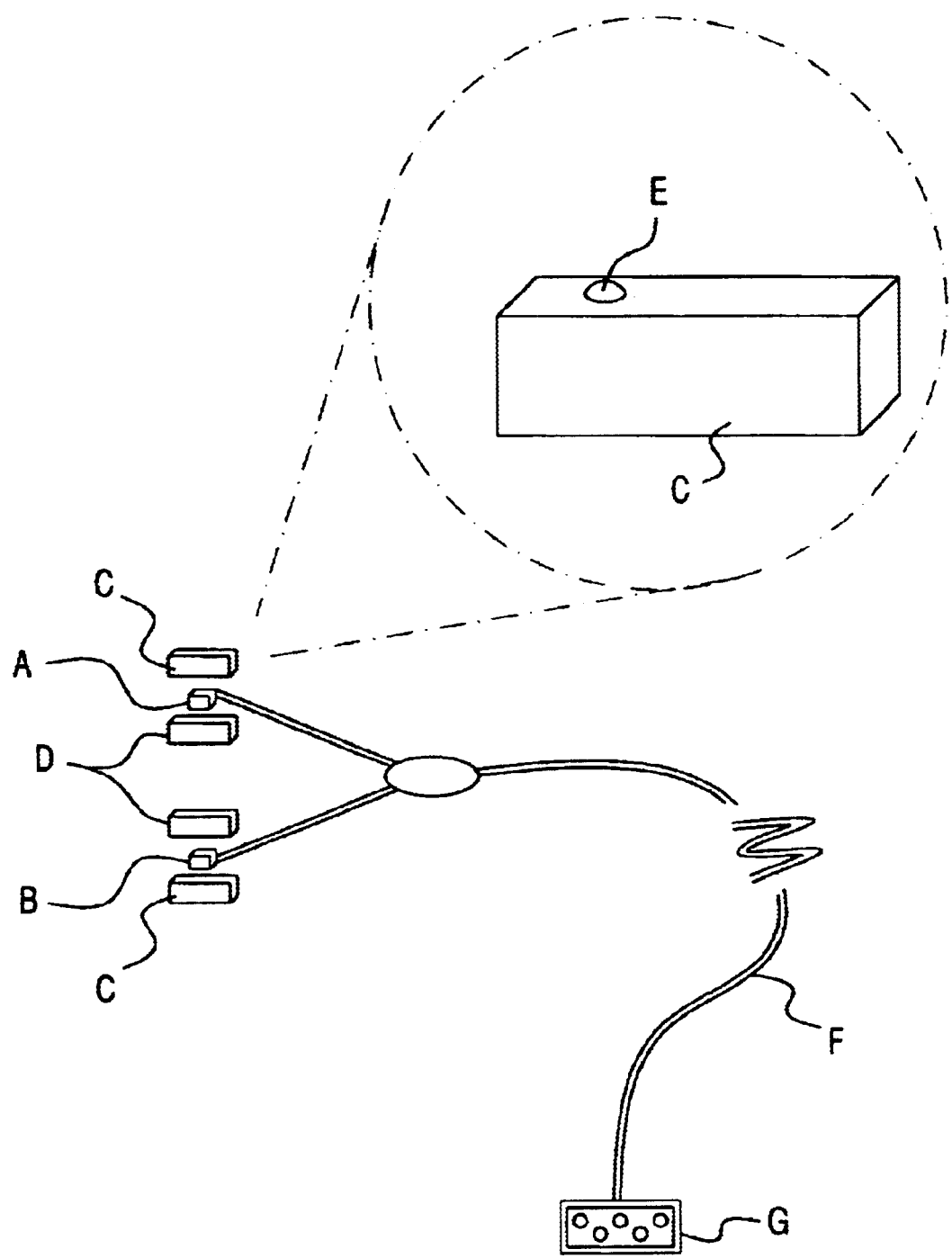
FIG. 1 is a exploded view of a pulse oximeter probe incorporating modular plastic housings.

The Modular Pulse Oximeter Probe consists of a "Y" type probe assembly in which the Light Emitting Diode (FIG. 1, Item A) and the Photocell Detector (FIG. 1, Item B) are incorporated into modular plastic housings. Said housings have an aperture or radiation transparent window incorporated therein so that said emitter and detector may be in communication with each other when said windows are in alignment with each other. In this preferred embodiment the modular housings consist of two half shells which encapsulate each the emitter and detector, one side of said shells (FIG. 1, Items C) being fabricated of an opaque plastic material and the other half of said shells (FIG. 1, Items D) being fabricated of a radiation transparent plastic material. The housings are designed in order to accommodate at least one of a possible multiplicity of manufacturers' light emitting diodes and photocell detectors. The housings may also contain an indentation (FIG. 1, Items E) into which a locking lever of the receptacles of the disposable bandage apparatus or reusable finger attachment device may lodge in order to secure the probe housings to the receptacles of the preferred attachment device. The cable (FIG. 1, Item F) and the connector (FIG. 1, Item G) of the probe may also be interchanged in order to be compatible with a multiplicity of different manufacturers' oximeters.

DESCRIPTION OF THE DISPOSABLE BANDAGE APPARATUS

Figure 2:
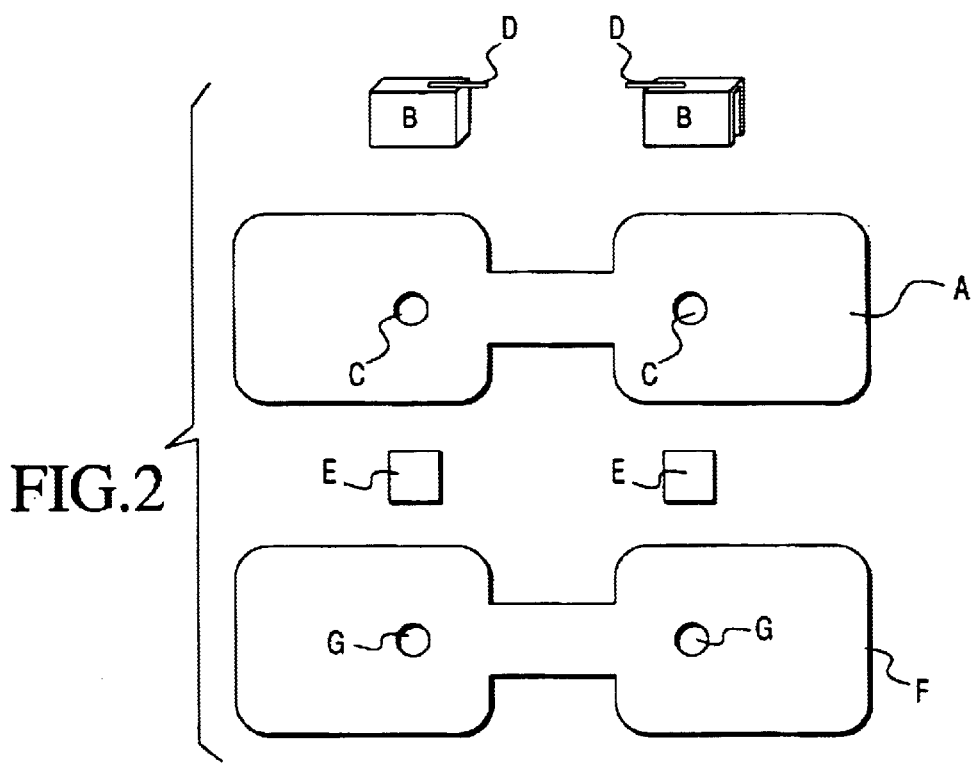
FIG. 2 is an exploded view of a disposable bandage apparatus incorporating modular plastic receptacles.
Figure 3:
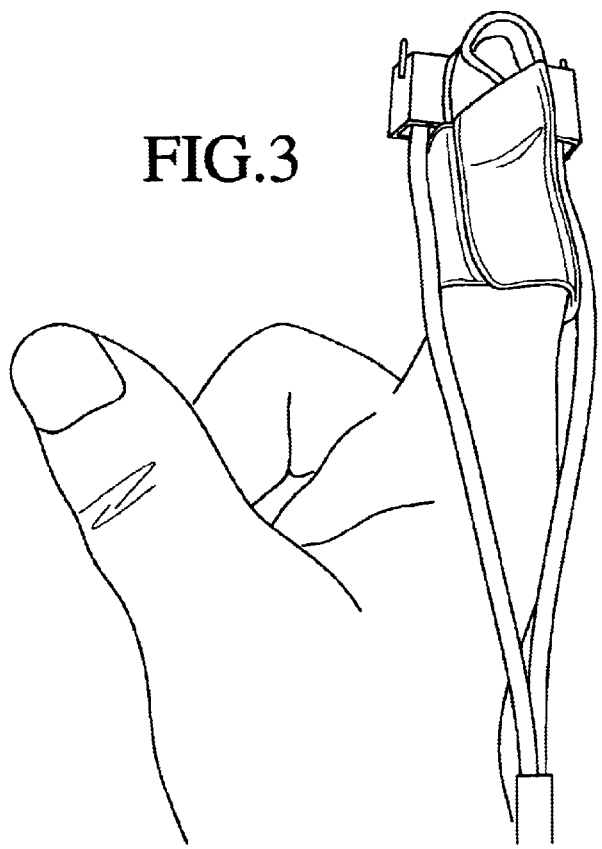
FIG. 3 is a view of the disposable bandage apparatus with the probe engaged and in use on the appendage of a patient.

The disposable bandage apparatus consists of at least one adhesive bandage strip (FIG. 2, Item A) wherein at least two receptacles (FIG. 2, Items B) are mounted on said strip. Said receptacles are mounted over apertures in the strip (FIG. 2, Items C) so that these apertures may diametrically oppose each other when the bandage strip is wrapped over the end of a patient's appendage. The Receptacles of the Disposable Bandage Apparatus may also incorporate locking levers (FIG. 2, Items D) that are intended to engage the indentations in the housings of the probe (FIG. 1, Items E) thus securing the probe housings within the bandage receptacles. The apparatus may also contain a radiation transparent window (FIG. 2, Items E) for isolation of the probe housings from the patient and may also incorporate an additional foam strip (FIG. 2, Item F) with apertures (FIG. 2, Items G) for cushioning the patient's appendage from the radiation transparent windows. FIG. 3 illustrates the disposable bandage apparatus with an engaged probe as it would appear in use on a human appendage.

DESCRIPTION OF THE REUSABLE FINGER ATTACHMENT DEVICE

Figure 4:
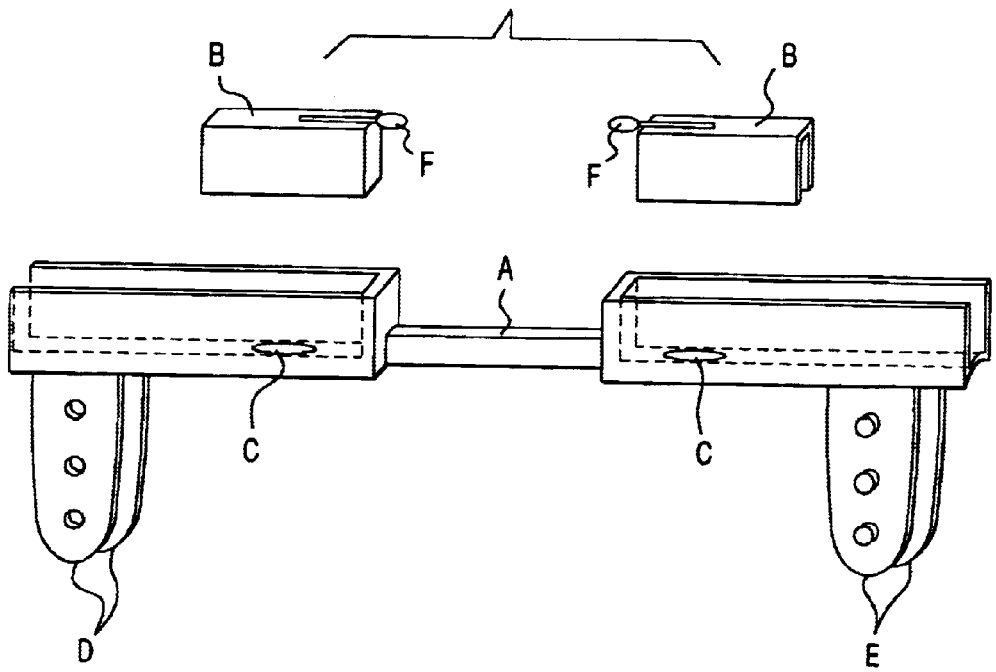
FIG. 4 is an exploded view of a reusable finger attachment device incorporating modular plastic receptacles.
Figure 5:
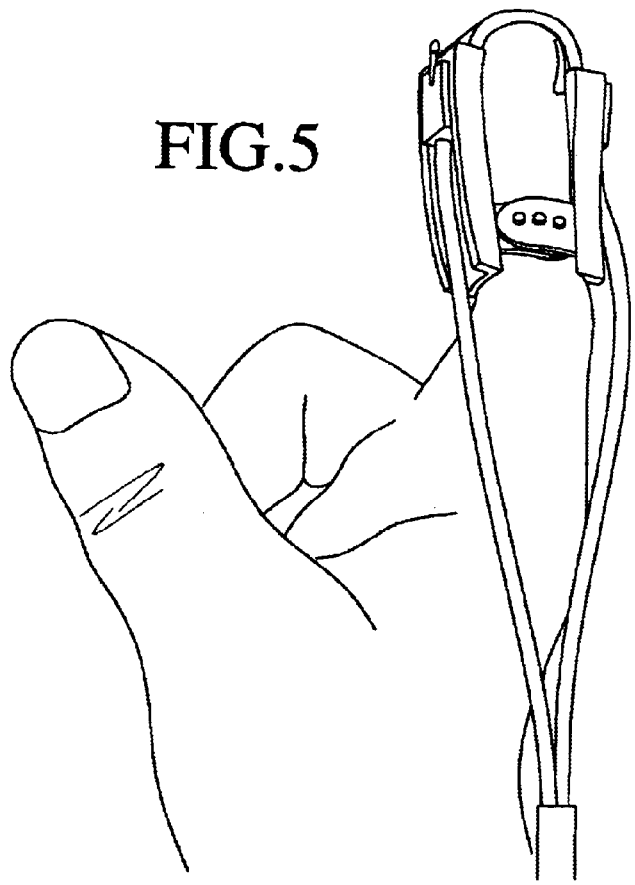
FIG. 5 illustrates the reusable finger attachment device, with the probe engaged, and in use on a human appendage.

The preferred embodiment of the Reusable Finger Attachment Device comprises a flexible plastic or foam strip (FIG. 4, Item A) with two receptacles (FIG. 4, Items B) mounted thereon. Said receptacles are mounted over apertures in the strip (FIG. 4, Items C) so that these apertures may diametrically oppose each other when the bandage strip is wrapped over the end of a patient's appendage. The strip also incorporates two perforated tabs (FIG. 4, Items D) and two additional tabs with molded knobs (FIG. 4, Items E ) so that when the strip is looped over a human digit, the tabs with the perforations overlay the tabs with the knobs and these, when pressed together, can adjustably and removably interlock with each other for securing the device to a human digit. The Receptacles of the Reusable Finger Attachment Device may also incorporate locking levers (FIG. 4, Items F) that are intended to engage the indentations in the housings of the probe (FIG. 1, Items E) thus securing the probe housings within the bandage receptacles. FIG. 5 illustrates the device as it would appear in use on a patient with the probe housings engaged in the Reusable Finger Attachment Device.

Other Fastening Means

As can be appreciated there are many means of fabricating either the Disposable Bandage Apparatus and Reusable Finger Attachment Device using modular receptacles into which a universal modular probe housing could be lockingly engaged. While these devices may offer the most efficient method fabrication and/or user friendliness, they are by no means exhaustive.

Method of Use

Whether using the Disposable Bandage Apparatus or the Reusable Finger Attachment Device, the methods of use are essentially the same. With either apparatus, the end of the human appendage is wrapped by the device and, in the case of the Disposable Bandage Apparatus, the adhesive strip simply sticks to the skin of the patient. With the Reusable Finger Attachment Device, the tabs containing the perforations and knobs are simply overlaid and pushed together thus securing the device to the digit. With either device the probe housings are pushed into the receptacles of the device and are locked into place by the locking levers that engage the indentations in the probe housings. When the monitoring of the patient is complete, the locking levers of the receptacles of either device are lifted in order to release the probe housings and the probe is removed from the device. In the event that a Disposable Bandage Apparatus is in use, it is then thrown away after the probe has been removed. When a Reusable Finger Attachment Device is in use, it may be removed, washed, and reused on another patient.

ADVANTAGES OF THE PRESENT INVENTION

1. The standardization of probes within a hospital whereby a multiplicity of manufacturers' oximeters could utilize probes having housings of the same size for engaging either reusable or disposable attachment devices is very favorable.
2. Finger attachment devices on the market today are hard wired to the probes, and when breakage occurs on the finger clip, the entire probe must be repaired or thrown away. With the present invention, when breakage occurs in either the finger attachment device or the probe itself, only the broken component has to be replaced.
3. A big problem exists with maintaining the cleanliness of reusable finger clips because the electronics are not removable from the finger clip and the device cannot be immersed or cleaned. With the present invention, the Reusable Finger Attachment Device can be removed from the probe and cleaned or sterilized.

While the invention has been described in relation to preferred embodiments of the invention, it will be appreciated that other embodiments, adaptations and modifications of the invention will be apparent to those skilled in the art.

What is claimed is:

1. A pulse oximeter probe system comprising a probe having at least one light emitting diode and at least one photocell detector wherein said emitter and detector are incorporated into modular plastic housings, at least one housing having an aperture or radiation transparent window aligned with said diode, and at least a second housing having an aperture or radiation transparent window aligned with said detector; a selected one of:

(a) a reusable finger attachment device having a first modular receptacle pair mounted thereon, or (b) a disposable bandage device having a second modular receptacle pair mounted thereon;

wherein respective ones of said housings can lockingly engage and disengage respective ones of said modular receptacles and transmit and receive light through the appendage of a patient when the selected one of the above devices (a) or (b) is attached to a patient and when the respective housings of said probe are matedly engaged with the respective receptacles of the attached device; and the receptacles of the disposable bandage device or the reusable finger attachment device have locking levers for lockingly engaging and disengaging said modular probe housings, respectively.

2. The probe system of claim 1 in which said housings have indentations for lockingly engaging and disengaging the levers of receptacles of a disposable bandage apparatus or reusable finger attachment device.

3. The probe system of claim 1 wherein said disposable bandage apparatus incorporates radiation transparent windows for the isolation of the probe housings from the patient.

4. The probe system of claim 1 in which the probe housings of probes to be used on a multiplicity of manufacturers' oximeters are adapted to be matedly engaged with a selected reusable finger attachment device or a disposable bandage apparatus having receptacles designed to mate with said probe housings.

5. A reusable finger attachment device for use with a pulse oximeter probe incorporating modular housings, comprising said attachment device incorporating modular receptacles for matingly engaging said modular probe housings; wherein the receptacles of the reusable finger attachment device have locking levers for lockingly engaging and disengaging said modular probe housings.

6. The reusable finger attachment device of claim 5 which said modular probe housings are adapted to be removed from said reusable finger attachment device in order to clean or sterilize said reusable finger attachment device.

7. A method of standardizing probes comprising designing probe housings to be matingly engageable with modular receptacles of a disposable bandage apparatus and a reusable finger attachment device and further constructing said probe housings to be incorporated into probes adapted to work with at least one of a multiplicity of manufacturers' oximeters.

* * * * *